(12) United States Patent
Davis et al.

(10) Patent No.: US 7,682,561 B2
(45) Date of Patent: *Mar. 23, 2010

(54) NEEDLELESS HUB DISINFECTION DEVICE AND METHOD

(75) Inventors: Gregory T. Davis, Crystal Lake, IL (US); Lawrence G. Ponsi, Wheeling, IL (US); Jeffrey B. Steffens, Cary, IL (US); Paul H. Hanifl, Barrington Hills, IL (US)

(73) Assignee: Sage Products, Inc., Cary, IL (US)

( * ) Notice: Subject to any disclaimer, the term of this patent is extended or adjusted under 35 U.S.C. 154(b) by 979 days.

This patent is subject to a terminal disclaimer.

(21) Appl. No.: 11/132,902

(22) Filed: May 19, 2005

(65) Prior Publication Data

US 2009/0175759 A1    Jul. 9, 2009

(51) Int. Cl.
*A61L 2/00* (2006.01)

(52) U.S. Cl. .................... 422/28; 442/292; 604/905

(58) Field of Classification Search ........ 604/905, 604/288.01, 164.04, 28, 199; 422/26, 44, 422/28, 292–302
See application file for complete search history.

(56) References Cited

U.S. PATENT DOCUMENTS

| | | | | |
|---|---|---|---|---|
| 1,152,286 A | * | 8/1915 | Brownson | 220/822 |
| 1,282,679 A | * | 10/1918 | Druskin | 222/142.9 |
| 2,582,109 A | * | 1/1952 | de Fee | 220/502 |
| 3,160,327 A | * | 12/1964 | Porcelli | 222/153.07 |
| 3,458,080 A | * | 7/1969 | Laurizio | 220/258.2 |
| 4,334,551 A | * | 6/1982 | Pfister | 137/614.03 |
| 4,346,703 A | * | 8/1982 | Dennehey et al. | 604/406 |
| 4,432,764 A | * | 2/1984 | Lopez | 604/533 |
| 4,440,207 A | * | 4/1984 | Genatempo et al. | 150/154 |
| 4,551,146 A | * | 11/1985 | Rogers | 604/403 |
| 4,573,983 A | * | 3/1986 | Annis | 604/322 |
| 4,624,664 A | * | 11/1986 | Peluso et al. | 604/256 |
| 4,642,091 A | * | 2/1987 | Richmond | 604/29 |
| 4,810,241 A | * | 3/1989 | Rogers | 604/28 |
| 4,919,658 A | * | 4/1990 | Badia | 604/265 |
| 4,921,491 A | * | 5/1990 | Champ | 604/199 |
| 4,983,161 A | * | 1/1991 | Dadson et al. | 604/28 |
| 5,053,003 A | * | 10/1991 | Dadson et al. | 604/28 |
| 5,056,464 A | * | 10/1991 | Lewis | 119/6.8 |
| 5,195,957 A | * | 3/1993 | Tollini | 604/29 |
| 5,301,849 A | * | 4/1994 | Guglielmini et al. | 222/517 |
| 5,332,113 A | * | 7/1994 | Kusler et al. | 215/249 |
| 5,435,358 A | * | 7/1995 | Kempka et al. | 141/312 |
| 5,531,810 A | * | 7/1996 | Fullemann | 96/105 |
| 5,536,258 A | * | 7/1996 | Folden | 604/265 |
| 5,554,135 A | | 9/1996 | Menyhay | |
| 5,792,120 A | | 8/1998 | Menyhay | |
| 5,875,942 A | * | 3/1999 | Ohmi et al. | 222/556 |

(Continued)

*Primary Examiner*—Kevin C Sirmons
*Assistant Examiner*—Michael J Anderson
(74) *Attorney, Agent, or Firm*—Barnes & Thornburg LLP

(57) ABSTRACT

A device for automatically disinfecting a portion of a medical implement, such as a needless hub or injection port. The device includes a body shaped to engage the medical implement with the portion to be disinfected exposed. A disinfectant pad is mounted on the body to permit displacement of the pad relative to the body and is biased such that when the pad is displaced from a rest position, the pad is urged toward the portion to be disinfected to contact and disinfect it.

16 Claims, 5 Drawing Sheets

U.S. PATENT DOCUMENTS

| | | | |
|---|---|---|---|
| 5,894,015 A * | 4/1999 | Rechtin | 422/301 |
| 5,921,425 A * | 7/1999 | Markey | 220/254.4 |
| 5,971,965 A * | 10/1999 | Mayer | 604/249 |
| 6,045,539 A | 4/2000 | Menyhay | |
| 6,113,068 A * | 9/2000 | Ryan | 251/149.4 |
| 6,207,201 B1 * | 3/2001 | Piacenza | 424/665 |
| 6,299,131 B1 * | 10/2001 | Ryan | 251/149.1 |
| 6,648,158 B1 * | 11/2003 | Lawrence | 215/306 |
| 6,706,022 B1 | 3/2004 | Leinsing | |
| 6,732,876 B2 * | 5/2004 | Belcastro | 220/253 |
| 6,875,205 B2 * | 4/2005 | Leinsing | 604/414 |
| 7,100,890 B2 * | 9/2006 | Cote et al. | 251/149.1 |
| 7,198,611 B2 * | 4/2007 | Connell et al. | 604/30 |
| 7,232,419 B2 * | 6/2007 | Castellanos | 604/29 |
| 2003/0105452 A1 * | 6/2003 | Mayer | 604/533 |
| 2003/0153865 A1 * | 8/2003 | Connell et al. | 604/28 |
| 2003/0229312 A1 * | 12/2003 | Smith et al. | 604/152 |
| 2004/0215170 A1 * | 10/2004 | Phung et al. | 604/540 |
| 2005/0017380 A1 * | 1/2005 | Namespetra et al. | 261/75 |
| 2006/0270990 A1 * | 11/2006 | Fangrow | 604/164.04 |
| 2007/0106205 A1 * | 5/2007 | Connell et al. | 604/29 |
| 2008/0095680 A1 * | 4/2008 | Steffens et al. | 422/300 |

* cited by examiner

NEEDLELESS HUB DISINFECTION DEVICE AND METHOD

BACKGROUND OF THE INVENTION

This invention relates to medical implements such as needleless hubs or injection ports, and in particular to a device for automatically disinfecting a portion of the medical implement and that keeps the hub and/or port covered, clean and disinfected.

Needleless vascular catheter hubs and access or injection ports are used thousands of times each day in the United States medical facilities. Unless the hubs and ports are disinfected, patients are at a significant risk of blood stream infections caused by microbes that gain access through the needleless hub or injection port.

In the past, practitioners using a needleless hub or injection port have sought to disinfect the hub or port with alcohol in order to prevent microbial entry. Practitioners who seek disinfection in this manner typically wipe the hub or injection port with an alcohol-soaked swab before accessing it. That, however, has proven to be only partially successful in reducing blood stream infections which are introduced through the needleless hubs or injection ports.

U.S. Pat. Nos. 5,554,135, 5,792,120 and 6,045,539 deal with the infection problem by providing a cover for the injection port, with the cover including a sponge and shatterable plastic capsule containing an antiseptic solution. When the cover is applied to a needleless hub or injection port and the plastic capsule is shattered, disinfectant soaks the sponge and disinfects the covered end of the needleless hub or injection port.

All disinfection procedures, including that of the patents of the immediately preceding paragraph, suffer a common infirmity. For disinfection to take place, a practitioner must actively take action, such as wiping the hub or injection port, or applying a disinfectant cap. No device has been provided which is automatic, each time the needleless hub or injection port is accessed, to disinfect the hub or port. That is, the devices have no means of "forced compliance", where the practitioner need do nothing to disinfect the hub or port other than access it.

SUMMARY OF THE INVENTION

The invention is directed to a device and method for automatically disinfecting a portion of a medical implement, such as a needleless hub or injection port, having forced compliance. The device comprises a body shaped to engage the medical implement with the portion to be disinfected exposed. A disinfectant pad is connected to the body, and a mounting is provided for the pad to permit displacement of the pad relative to the body. A resilient device biases the pad such that when the pad is displaced from a rest position, where it is disinfecting the hub or port, or keeping said hub or port disinfected, the pad is urged toward the portion to be disinfected to contact and disinfect that portion.

In accordance with the preferred form of the invention, the body includes an aperture shaped to accommodate the needleless hub or injection port. In one form of the invention, the mounting for the pad comprises a slide, with the slide being movably secured to the body. In one embodiment, the resilient device comprises at least one spring. In another embodiment, the resilient device comprises an elastic band.

In a further form of the invention, the mounting for the pad comprises a cowl which is pivotally secured to the body. The resilient device comprises a torsion spring which, when the cowl is displaced, returns the cowl to the rest position.

In all forms of the invention, preferably a cover for the pad is provided to help maintain the disinfectant in the pad. The rest position for the pad can be coincident with the location of the portion of the medical implement which is to be disinfected, or the rest position can be located to one side of that portion such that when the pad is displaced from the rest position, the pad is urged toward the portion to be disinfected in order to contact and disinfect it.

In accordance with the method according to the invention, the disinfectant pad is located at a rest position proximate the portion to be disinfected. The pad is biased such that when the pad is displaced from the rest position, the pad returns to the rest position and contacts and disinfects the portion to be disinfected automatically. Disinfection can be when the pad is displaced, when the pad returns to the rest position, or both.

BRIEF DESCRIPTION OF THE DRAWING

The invention is described in greater detail in the following description of examples embodying the best mode of the invention, taken in conjunction with the drawing figures, in which.

DESCRIPTION OF EXAMPLES EMBODYING THE BEST MODE OF THE INVENTION

Figure 1:
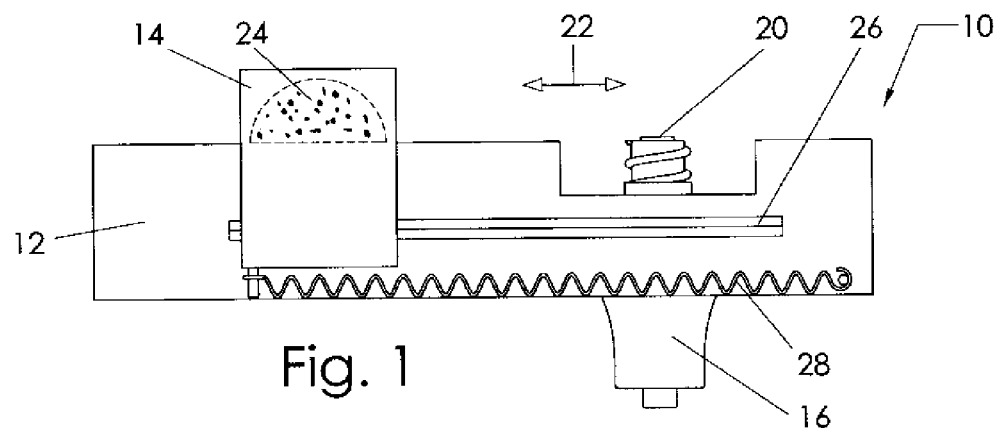
FIG. 1 is a side elevational illustration of one form of the invention, with the slide displaced, permitting access to the medical implement upon which the device is mounted.

A first form of the device according to the invention is shown generally at 10 in FIG. 1. The device 10 includes two primary components, a body 12 and a slide 14.

Figure 3:
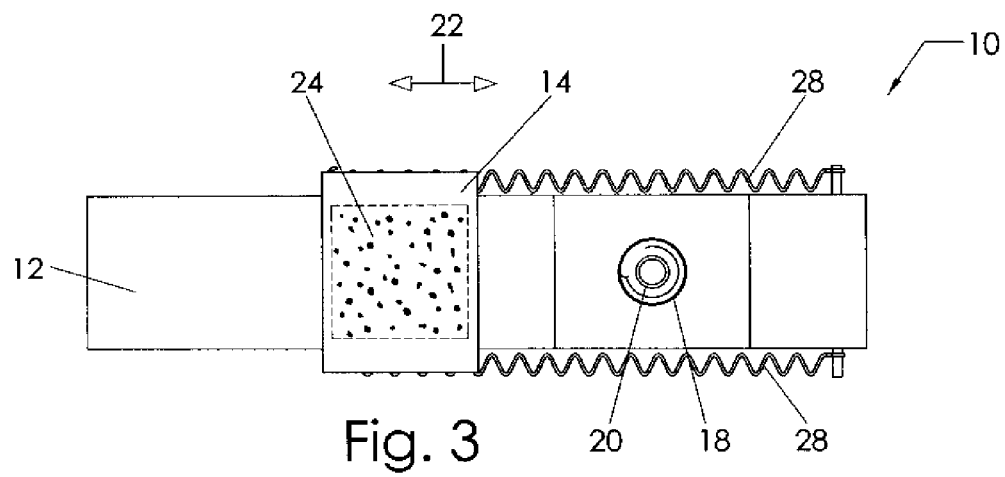
FIG. 3 is a top plan of the device of FIG. 1, showing the slide partially displaced, exposing the medical implement.

The body 12 is shaped to engage a medical implement 16, the medical implement 16 preferably comprising a needleless hub or injection port. The body 12 include an aperture 18, as best shown in FIG. 3, through which the medical implement 16 extends. Typically the medical implement 16 is topped with a head 20, through which access is provided, either for withdrawing fluid or injection therewithin to a vascular catheter (not illustrated) connected to the medical implement 16 in a conventional manner. The medical implement 16 and its use are well known in the art, and are not described in greater detail.

Figure 2:
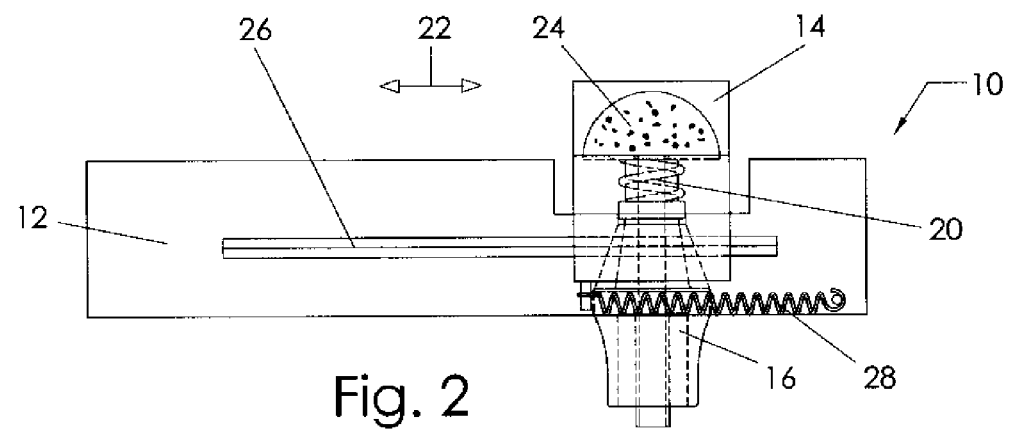
FIG. 2 is a side elevational illustration similar to FIG. 1, but with the slide in a rest position.

The slide 14 is mounted on the body 12 for translation to and fro, as depicted by the arrow 22 in FIGS. 1 through 3. The slide 14 comprises a mounting for a disinfectant pad 24 mounted therewithin. The slide 14 also is a cover for the disinfectant pad to help prevent disinfectant solution impregnating the pad 24 from being lost, such as through evaporation.

The slide 14 is appropriately mounted on the body 12 so that the slide can be displaced from a rest position shown in FIG. 2 to a position exposing the head 20, as shown in FIGS. 1 and 3. To this end, the slide 14 can be mounted in a track or groove 26 formed in opposite sides of the body 12. Not only does the track or groove 26 then locate the slide 14 on the body 12, but also the track or groove 26 defines extremes of translation of the slide 14 along the body 12.

The slide 14 is biased to the rest position shown in FIG. 2 by means of opposite extension springs 28. While a single spring 28 on one side of the body 12 may be adequate for proper balancing of the force supplied to the slide 14, it is preferred that one spring 28 be located on each side of the body 12. When the slide 14 is displaced as shown in FIGS. 1 and 3, the tensioning of the springs 28 increases, urging the slide 14 to the rest position shown in FIG. 2 with the disinfectant pad 24 located over the head 20. A center mounted spring may also be used to return the slide to the rest position in FIG. 2, in place of the side springs 28.

In operation, when the device 10 is secured to a medical implement 16 such as a needleless hub or injection port, in the rest position, the slide 14 is in the position shown in FIG. 2, with the disinfectant pad 24 in position over, and disinfecting, the head 20. When access to the medical implement is desired, a user moves the slide 14 as shown in FIGS. 1 and 3 to expose the head 20. Then, in a conventional fashion, the medical implement 16 is accessed for use. Since the springs 28 are under tension, the slide 14 must be held in the displaced position shown in FIGS. 1 and 3, and once use of the medical implement 16 has been completed, the slide 14 is then released to return to the rest position shown in FIG. 2, disinfecting the head 20.

Various alternatives to that shown in FIGS. 1 through 3 are possible, while still falling within the scope of the invention. For example, when the slide 14 is in the rest position, the disinfectant pad 24 can be located to one side of the head 20, and only when the slide 14 is displaced could the disinfectant pad 24 contact the head 20 for disinfecting purposes. Other alternatives will be equally as evident.

Figure 4:
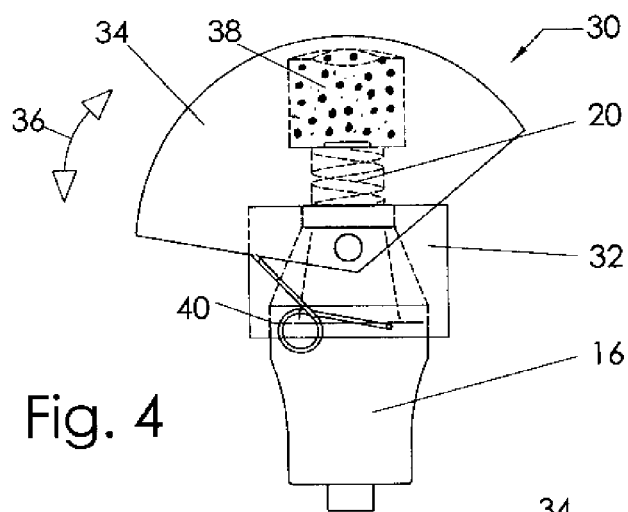
FIG. 4 is a side elevational illustration of a second embodiment of the invention having a pivotal cowl.
Figure 5:
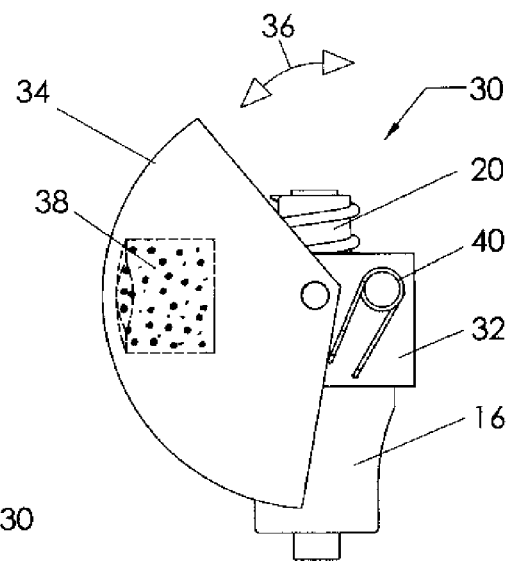
FIG. 5 is a side elevational illustration similar to FIG. 4, but with the cowl displaced.
Figure 6:
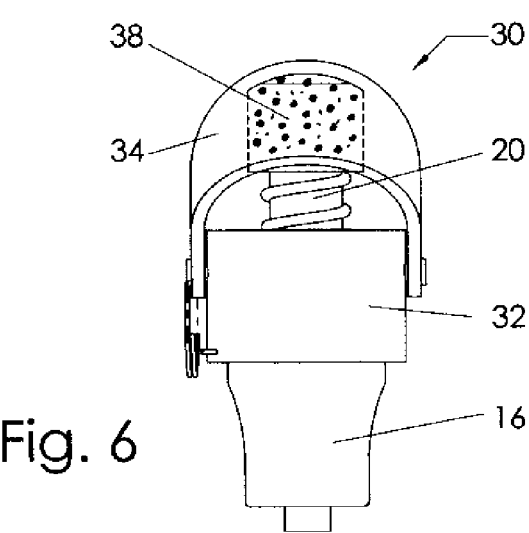
FIG. 6 is an end elevational illustration of the second embodiment of FIG. 4.

Another form of the invention is shown in FIGS. 4 through 6. The medical implement 16 remains the same, and therefore bears the same reference character.

In this form of the invention, the device 30 includes a collar 32 on the medical implement 16. Instead of a slide such as the slide 14 of the embodiment of FIGS. 1 through 3, a cowl 34 is pivotally mounted on the collar 32, the pivoting action of the cowl 34 being indicated by the arrow 36. A disinfectant pad 38 is located in the cowl 34, and in the rest position shown in FIGS. 4 and 6, the disinfectant pad 38 is seated over the head 20.

A torsion spring 40 biases the cowl 34 to the rest position shown in FIGS. 4 and 6. Similar to the embodiment of FIGS. 1 through 3, a pair of torsion spring 40 can be utilized, on opposite sides of the collar 32. When the cowl 34 is displaced from the rest position shown in FIGS. 4 and 6 to an operative position shown in FIG. 5, the torsion spring 40 seeks to urge the cowl 34 to the rest position shown in FIGS. 4 and 6, and thus, when displaced, the cowl 34 must be maintained in some fashion in the opened orientation shown in FIG. 5, or it will return to the rest position shown in FIGS. 4 and 6.

A further form of the device according to the invention is shown at 50 in FIGS. 7 through 10. Again, the device 50 is shown with its body 52 mounted on a conventional medical implement 16, the implement 16 therefore not being described in greater detail.

Figure 7:
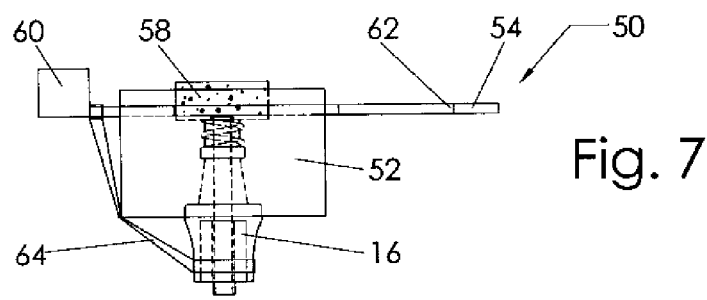
FIG. 7 is a side elevational illustration of another embodiment of the invention, with the slide in the rest position.
Figure 8:
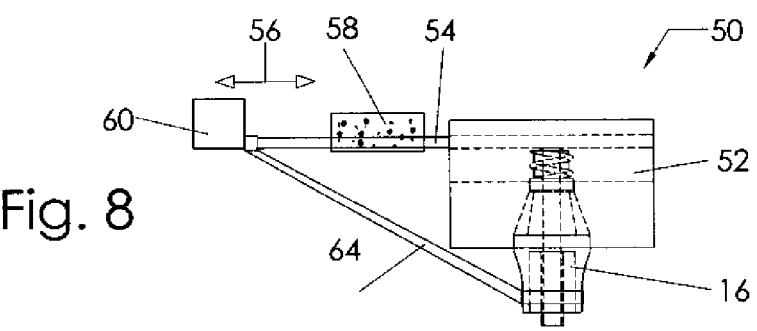
FIG. 8 is a side elevational illustration similar to FIG. 7, but with the slide displaced.
Figure 9:
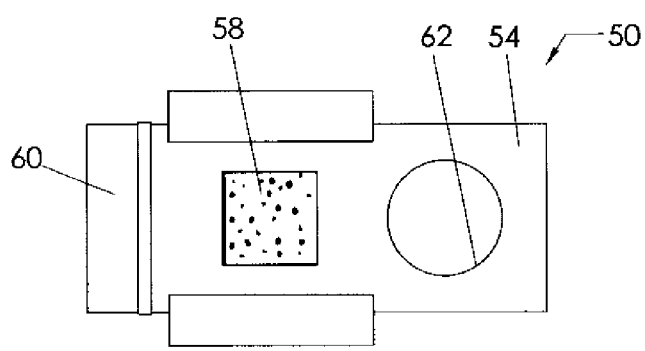
FIG. 9 is a top plan view of the device of FIG. 7.
Figure 10:
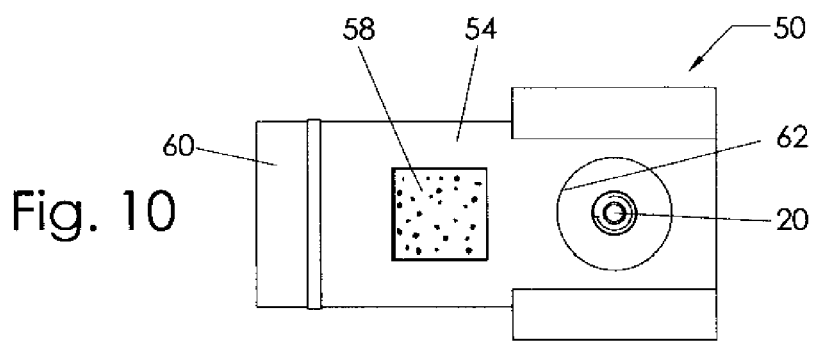
FIG. 10 is a top plan view of the device shown in FIG. 8.

In this form of the invention, a slide 54 is mounted for translation on the top of the body 52 between a rest position shown in FIGS. 7 and 9 and a displaced position shown in FIGS. 8 and 10. The translation of the slide 54 is depicted by the arrow 56.

In this form of the invention, the slide 54 carries a disinfectant pad 58 which, in the rest position, is located above and disinfecting the head 20. While shown exposed for explanation purposes, normally the disinfectant pad 58 would be appropriately covered to protect it and the disinfectant solution that it carries.

The slide 54 also includes a knob 60, engageable by the user to facilitate displacement of the slide 54. Also, the slide 54 includes an aperture 62 which, when the slide is fully displaced to the orientation shown in FIGS. 8 and 10, is coincident with the head 20 of the medical implement 16, thus allowing conventional access to the medical implement 16. The slide 54 otherwise prevents access to the medical implement 16.

Similar to the embodiments of FIGS. 1 through 6, a resilient device in the form of an elastic band 64 extends between the slide 54 and the body 52. When the slide 54 is displaced as shown in FIGS. 8 and 10, the elastic band 64 urges the slide 54 to the rest position shown in FIGS. 7 and 9, and therefore the slide 54 must be retained against the force of the elastic band 64 in the opened or operative position shown in FIGS. 8 and 10 for access to the medical device 16 via the aperture 62 to be possible.

Other forms of elasticity for the resilient device can be employed, other than a spring or an elastic band, as will be evident to one skilled in the art. For example, rebounding plastic, such as a living hinge, or other types of bands, such as polymer bands, can be used.

Another version of the invention is illustrated in FIGS. 11 through 14. In this form of the invention, the device 70 is, similar to the other embodiments of the invention, shown mounted with its body 72 secured on a conventional medical implement 16.

Figure 11:
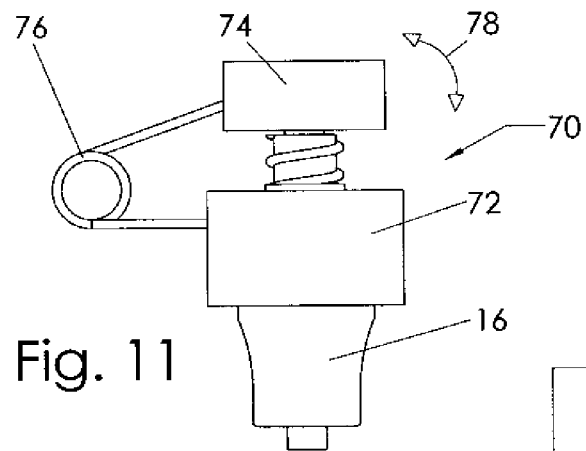
FIG. 11 is a side elevational illustration of another embodiment of the invention, with the disinfectant pad in a rest position.
Figure 13:
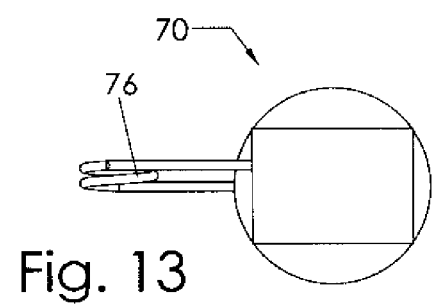
FIG. 13 is a top plan view of the disinfectant pad of FIGS. 11 and 12.

In this form of the invention, in the rest position shown in FIGS. 11 and 13, a cowl 74 is seated on the top of the medical implement 16. Similar to the earlier forms of the invention, the cowl 74 includes a disinfectant pad therewithin for disinfecting the medical implement 16 each time the cowl 74 returns to the rest position.

Figure 12:
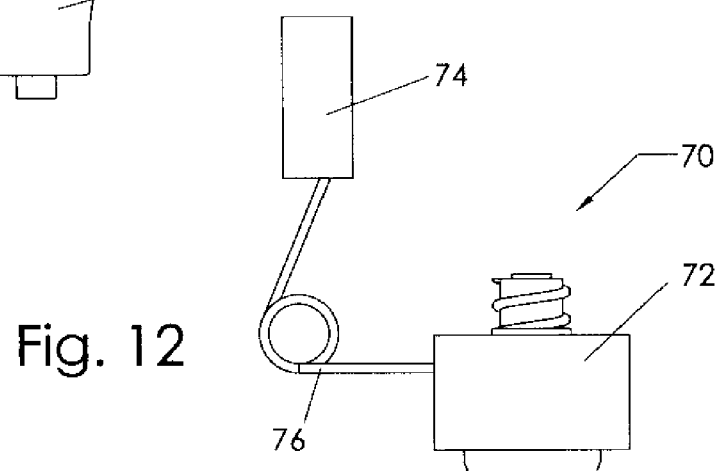
FIG. 12 is a side elevational illustration of the embodiment of FIG. 11, with the disinfectant pad displaced.
Figure 14:
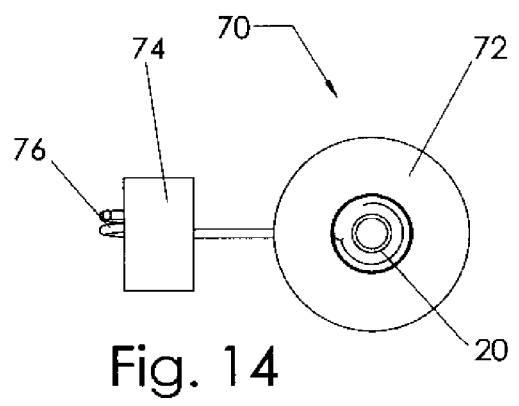
FIG. 14 is a top plan view of the device as shown in FIG. 12.

The cowl 74 is maintained in place in relation to the body 74 by means of a torsion spring 76, and is pivotal against the force of the spring 76 as shown by the arrow 78. Thus, when the cowl 74 is displaced as shown in FIGS. 12 and 14 to permit operative access to the medical implement 16, the cowl 74 must be retained against the force of the torsion spring 76, or the cowl 74 will return to the rest position shown in FIGS. 11 and 13, thus protecting and disinfecting the medical implement 16.

Figure 15:
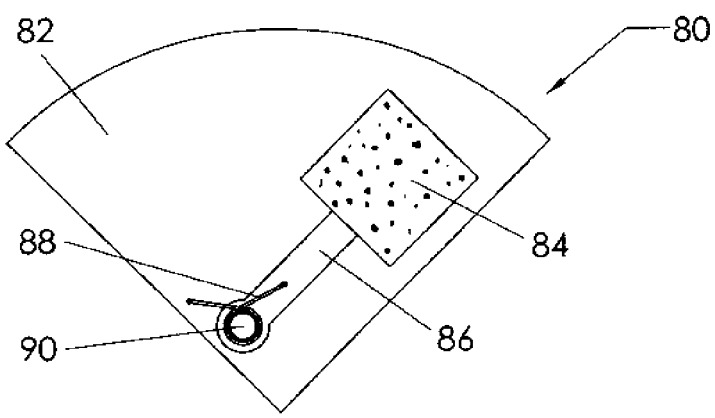
FIG. 15 is a top plan view of a further embodiment of the invention, with the disinfectant pad in a rest position.
Figure 16:
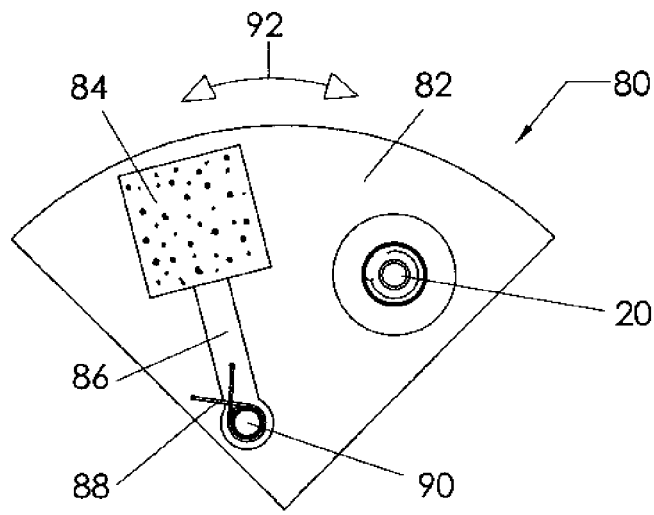
FIG. 16 is a view similar to that of FIG. 15, but with the disinfectant pad displaced.
Figure 17:
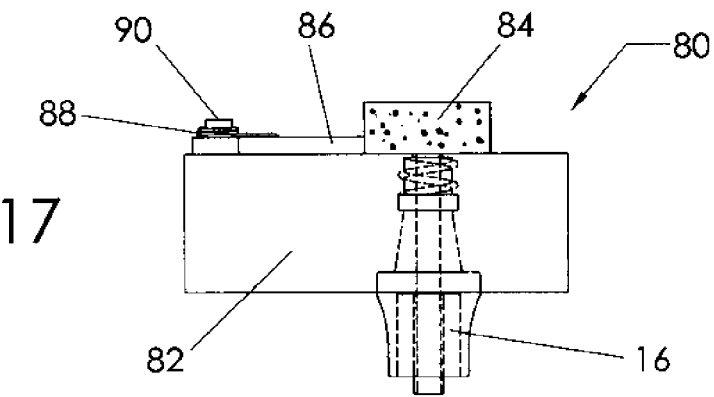
FIG. 17 is a side elevational illustration of the embodiment of FIG. 15.

Yet another version of the invention is illustrated in FIGS. 15 through 17. In this form of the invention, the device 80 is, similar to the other embodiments of the invention, mounted with its body 82 secured on a conventional medical implement 16.

In this form of the invention, in the rest position shown in FIG. 15, a disinfectant pad 84, mounted on a rotatable arm 86, is seated on the top of the medical implement 16. The pad 84 is maintained in place in the rest position shown in FIG. 15 by means of a torsion spring 88. The spring 88 is mounted about a pivot 90 for the rotatable arm 86, and bears against the arm 86 to maintain the pad 84 in the rest position shown in FIG. 15. When the arm 86 is pivoted against the force of the spring 88 as shown by the arrow 92, the head 20 of the medical implement 16 is not only disinfected, but exposed to the operative position shown in FIG. 16. The spring 88 urges the arm 86 to return to the rest position shown in FIG. 15 when the arm 86 is released, and therefore, as in the other embodiments of the invention, in order for the arm 86 to remain in the operative position shown in FIG. 16, the arm 86 must be retained against the force of the spring 88.

The invention provides several unique advantages. First, no matter what the form of the device according to the invention, there is always forced compliance where the medical implement is disinfected every time use of the medical implement is desired. The risk of infection is therefore greatly reduced.

Second, the port of the medical implement is always covered, except during a very brief transition period when access to the medical implement is sought.

Third, with full access to the medical implement being provided, compliance with any nursing protocols for swabbing of the port of the medical implement can easily be met.

Fourth, the device of the invention is readily adaptable to all types of fittings, with both male and female luer ends.

Various other advantages of the invention will be evident to those skilled in the art, and various changes can be made to the invention without departing from the spirit thereof or scope of the following claims.

What is claimed is:

1. A device for automatically disinfecting a portion of a medical implement, comprising
   a. a body shaped to engage the medical implement with the portion to be disinfected exposed,
   b. a disinfectant pad connected to said body,
   c. a mounting for said pad to permit displacement of said pad relative to said body, creating a gap between said pad and said portion to be disinfected, and
   d. a resilient device biasing said pad such that when said pad is displaced from a rest position, where it is proximate the portion to be disinfected, said pad is urged to return toward the portion to be disinfected to contact and disinfect the portion.

2. The device according to claim 1, in which said medical implement comprises a needleless hub or injection port, and said body includes an aperture shaped to accommodate said hub or injection port.

3. The device according to claim 1, in which said mounting comprises a slide, said slide being movably secured to said body.

4. The device according to claim 1, in which said resilient device comprises at least one spring.

5. The device according to claim 1, in which said resilient device comprises an elastic band.

6. The device according to claim 1, in which said mounting comprises a cowl pivotally secured to said body.

7. The device according to claim 6, in which said resilient device comprises a torsion spring.

8. The device according to claim 1, in which said mounting includes a cover for said pad.

9. The device according to claim 1, in which said rest position is coincident with location of the portion to be disinfected.

10. A device for automatically disinfecting a needleless hub or injection port, comprising,
    a. a body shaped to be mounted proximate an orifice of the needleless hub or injection port,
    b. a disinfectant pad associated with said body,
    c. a mounting for said pad to permit displacement of said pad relative to said body, creating a gap between said pad and said portion to be disinfected, and
    d. means biasing said pad such that when said mounting is displaced from a rest position, said mounting is urged toward said orifice so that said pad contacts and disinfects said orifice.

11. The device according to claim 10, in which said body includes an aperture shaped to accommodate said orifice.

12. The device according to claim 10, in which said mounting comprises a slide, said slide being movably secured to said body.

13. The device according to claim 10, in which said biasing means comprises at least one spring.

14. The device according to claim 10, in which said biasing means comprises an elastic band.

15. The device according to claim 10, in which said mounting comprises a cowl pivotally secured to said body.

16. The device according to claim 10, in which said biasing means comprises a torsion spring.

* * * * *